US009024020B2

(12) United States Patent
Schadt et al.

(10) Patent No.: US 9,024,020 B2
(45) Date of Patent: May 5, 2015

(54) HORIZONTAL HIGH-PRESSURE MELAMINE REACTOR

(75) Inventors: Arne Schadt, Pasching (AT); Robert Schlesinger, Linz (AT)

(73) Assignee: Casale SA, Lugano-Besso (CH)

( * ) Notice: Subject to any disclaimer, the term of this patent is extended or adjusted under 35 U.S.C. 154(b) by 25 days.

(21) Appl. No.: 13/806,157

(22) PCT Filed: Jun. 23, 2011

(86) PCT No.: PCT/EP2011/060553
§ 371 (c)(1),
(2), (4) Date: Mar. 21, 2013

(87) PCT Pub. No.: WO2011/161215
PCT Pub. Date: Dec. 29, 2011

(65) Prior Publication Data
US 2013/0172555 A1 Jul. 4, 2013

(30) Foreign Application Priority Data

Jun. 24, 2010 (EP) .................................... 10167186

(51) Int. Cl.
| | | |
|---|---|---|
| C07D 251/60 | (2006.01) | |
| C07D 251/62 | (2006.01) | |
| B01J 19/24 | (2006.01) | |
| B01J 3/04 | (2006.01) | |
| B01J 10/00 | (2006.01) | |
| B01J 4/00 | (2006.01) | |
| B01J 19/00 | (2006.01) | |

(52) U.S. Cl.
CPC ............ *B01J 10/005* (2013.01); *C07D 251/62* (2013.01); *B01J 3/042* (2013.01); *B01J 4/002* (2013.01); *B01J 10/00* (2013.01); *B01J 19/006* (2013.01); *B01J 19/24* (2013.01); *B01J 2219/00083* (2013.01); *B01J 2219/00101* (2013.01); *B01J 2219/00768* (2013.01); *B01J 2219/182* (2013.01); *B01J 2219/1943* (2013.01); *C07D 251/60* (2013.01)

(58) Field of Classification Search
CPC ..... C07D 251/60; C07D 251/62; B01J 19/24; B01J 3/04; B01J 10/00

USPC ................................................. 544/201, 203
See application file for complete search history.

(56) References Cited

U.S. PATENT DOCUMENTS

| | | | |
|---|---|---|---|
| 3,423,410 | A | 1/1969 | Takahashi et al. |
| 3,700,672 | A | 10/1972 | Kokubo et al. |
| 7,022,848 | B2 | 4/2006 | Bucka et al. |
| 2005/0038244 | A1 | 2/2005 | Bucka et al. |
| 2007/0060751 | A1 | 3/2007 | Schroder et al. |
| 2007/0232801 | A1 | 10/2007 | Bairamijamal |

FOREIGN PATENT DOCUMENTS

| | | |
|---|---|---|
| DE | 102006055571 A1 | 5/2008 |
| EP | 0612560 A1 | 8/1994 |
| EP | 0976724 A1 | 2/2000 |
| EP | 1296963 A1 | 4/2003 |
| EP | 1328520 B1 | 12/2007 |
| EP | 2119710 A1 | 11/2009 |
| FR | 1505343 | 12/1965 |
| FR | 1483116 | 6/1966 |
| GB | 1460029 | 12/1976 |
| WO | 9900374 A1 | 1/1999 |
| WO | 0202535 A1 | 1/2002 |
| WO | 0234730 A1 | 5/2002 |
| WO | 2004111016 A1 | 12/2004 |
| WO | 2006013079 A2 | 2/2006 |
| WO | 2008061704 A1 | 5/2008 |

OTHER PUBLICATIONS

Crews, G.M. et al., Melamine and Guanamines, Ullman's Encyclopedia of Industrial Chemistry, 6th Edition, 2003, pp. 2005-2221, vol. 21.

*Primary Examiner* — Venkataraman Balasubramanian
(74) *Attorney, Agent, or Firm* — The Webb Law Firm

(57) ABSTRACT

A high-pressure melamine reactor is provided. The high-pressure melamine reactor comprising at least one horizontal reactor body having a bottom and a top side with at least one dome integrally formed on the top side of the reactor body. The at least one horizontal reactor body comprises at least two compartments separated by at least one baffle, in particular an overflow baffle. The at least one dome is solely located above at least one of the compartments serving as melamine synthesis unit, wherein the at least one compartment serving as melamine synthesis unit comprises at least one heating element.

12 Claims, 2 Drawing Sheets

HORIZONTAL HIGH-PRESSURE MELAMINE REACTOR

CROSS-REFERENCE TO A RELATED APPLICATION

This application is a National Phase Patent Application of International Patent Application Number PCT/EP2011/060553, filed on Jun. 23, 2011, which claims priority of European Patent Application Number 10167186.5, filed on Jun. 24, 2010, the content of which are incorporated herein in its entirety.

BACKGROUND OF THE INVENTION

1. Field of the Invention

The present invention relates to a melamine reactor according to claim 1 and a process for obtaining melamine according to claim 13.

2. Description of the Prior Art

Melamine is usually obtained from urea in the presence of ammonia according to

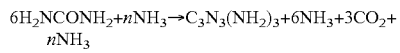

$$6H_2NCONH_2 + nNH_3 \rightarrow C_3N_3(NH_2)_3 + 6NH_3 + 3CO_2 + nNH_3$$

Thus for every mole of melamine three moles of $CO_2$ and six moles of $NH_3$ together with the introduced $NH_3$ in excess are obtained.

The industrial processes for melamine synthesis are mainly classified into a catalytic process at low pressures below 1 MPa and non-catalytic processes at high-pressures above 5 MPa (see Ullmann's Encyclopedia of Industrial Chemistry, 6th edition, Vol. 21, p. 205 ff).

In the following reference is being made to the high-pressure processes and in particular to the process steps carried out in the high-pressure part of a melamine plant.

At present the high-pressure melamine process starts out from pressurized molten urea at temperatures between 135 and 160° C. and is carried out in a pressure range between 5 and 20 MPa and a temperature range of 370 to 430° C.

The high pressure part comprises basically three sections, in which the following process steps are carried out:
endothermic reaction of urea to melamine,
separation of the offgas from the melamine melt, $CO_2$ removal by introducing ammonia gas in the melt and optionally aging of the melamine melt, and
washing or scrubbing the offgas.

These three different steps are performed in different sets of equipment separated from each other. The conversion of urea to melamine is carried out in a synthesis reactor with heating bundles. The obtained raw melamine melt is then transferred to a second reactor or stripping reactor in which the dissolved gases, in particular $CO_2$, are removed from the melamine melt by introducing gaseous ammonia in counter current, and where the melamine melt is allowed to reside for a certain time (Aging).

The offgases generated during the melamine synthesis reaction are usually removed in the upper part of the melamine reactor and then transferred to the scrubber. The raw melamine melt is introduced in the second reactor where ammonia gas is introduced in counter current for removing $CO_2$ from the melt which is also transferred to the scrubber. During the stripping in the second reactor the melamine melt is allowed to reside for a certain time (Aging).

In order to reduce the amount of side products, in particular melem and melam, liquid or gaseous ammonia can be introduced to the reaction melt. The ammonia is fed through a suitable inlet, in particular through a distributor, injector or nozzle.

The offgas is removed from the stripper and sent to a scrubber where the offgas is cooled, melamine present in the offgas is separated from the offgas, and in counter current the urea melt is preheated. The urea melt comprises fresh urea or circulating urea which is kept in circulation by a circulation pump. This urea circulation pump serves also for feeding the preheated urea melt to the high pressure melamine reactor. The excess heat in the scrubber is removed by an external heat exchanger. All in all, a conventional high pressure part of a melamine plant consists of approximate 5 different main pieces of equipment, in particular synthesis reactor, stripper, scrubber, heat exchanger and circulation pump, which are connected by a number of pipes.

Thus, this construction requires a number of different bulk materials like pipes including the proper insulation, and intensive heat tracing, valves, steel structures and more. Such a complex system of reactors, pipelines and valves is however difficult to operate and to maintain.

Considering that the applied pressure is above 5 MPa it is obvious that a reduction in bulk material, in particular a reduction of pipes and valves would minimize the risk of failure and would simultaneously reduce the costs for equipment (Capex) and maintenance and plant availability (Opex).

Thus, it would be desirable to simplify the construction of a high-pressure part of a melamine plant.

One possible approach is introducing specific improvements into the equipment design (U.S. Pat. No. 3,700,672) what however increases the overall investment costs.

Another approach is the combination of the different reaction steps e.g. melamine synthesis, stripping, scrubbing in one reactor. Such a reactor is for instance described in EP 612 560 A1. This high-pressure melamine reactor comprises three sections separated from each other by means of diaphragms: a top sector serving as washing or scrubbing sector, a central sector serving as stripping or separation sector, and a bottom sector serving as synthesis reactor. Each sector communicates with the other two sectors through pipelines.

However, this reactor still requires a number of different equipment like diaphragms, pipelines and valves making it vulnerable to corrosion by the processing fluids or melts and causing high costs.

SUMMARY OF THE INVENTION

Thus, it would be desirable to reduce the number of necessary pieces of equipment even further.

According to an exemplary embodiment of the invention y, the present high-pressure melamine reactor comprises at least one horizontal reactor body having a bottom and a top side with at least one dome integrally formed on the top side of the reactor body. The at least one horizontal reactor body comprises at least at least two compartments, which are separated by at least one baffle, in particular an overflow baffle. According to the invention the dome is arranged or located above one of the two compartments, more precisely above the compartment which serves as melamine synthesis unit.

Thus, the reactor is separated in two compartments which are in liquid communication with each other. One of the two compartments forms thereby an equivalent to the first reactor, e.g. melamine synthesis reactor, and the second compartment of the two forms an equivalent to the second reactor, e.g. stripper. Thus, the at least first compartment serves as a melamine synthesis unit and the second compartment serves as a stripping unit. The at least one dome serves as a scrubber unit including a heat exchanger.

The reactor according to the invention enables thus the conduction of three reaction steps, e.g. melamine synthesis, stripping the melamine melt from any excess of gas, in particular $CO_2$, and scrubbing the offgases in one piece of equipment instead in five conventionally used pieces. The present reactor allows for a narrow and complex design, less equipment and hence less bulk material. Due to the horizontal arrangement of the reactor the overall height is reduced.

Furthermore, due to the fact that the dome is placed above the compartment serving as the melamine reactor a high pressure urea circulation pump is no longer required since the urea melt flows into the reactor compartment by gravity. This results in significant savings in investment costs but also in a simplification of the whole high pressure part of the process as the urea circulation pump is usually a very complex and accident-sensitive equipment. Also the larger interface in the stripper compartment allows an improved mixing between melamine melt and the introduced ammonia. Overall the present reactor requires less investment costs and less operation costs compared to conventional operated high pressure parts of a melamine plant.

Furthermore, the inventive reactor design allows for a real two-step reaction wherein the residence time for each of the reaction steps can easily be adjusted by means of the fluid level in the respective compartment. Any back mixing is avoided so that the quantity of non-reacted compounds is extremely reduced in the reaction mixture.

In a preferred embodiment the dimensions, more precisely the diameter of the dome corresponds at least to the dimension or diameter of the compartment serving as melamine synthesis unit. Thus, it is preferred that the dimensions of the dome such width or diameter are the same or less than the dimensions as width or diameter of the melamine synthesis compartment. This means that the dome is arranged solely above one compartment and thus covers fully or partially only the one compartment and does not extend over more than the one compartment.

The overall length of the horizontal reactor can be between 5 and 15 m, preferably between 7 m and 13 m, in particular preferably between 9 and 11 m.

The dome may comprise at least one inlet for urea melt, at least one outlet for off gases and at least one heat exchanger. The dome is preferably located above the area of the first compartment of the body reactor used for melamine synthesis so that the offgases released during the reaction of urea to melamine move continuously upwards into the dome and are being scrubbed and freed there from melamine in counter flow by the incoming urea melt. The offgases are thereby washed, cooled and finally released and reused for instance in urea production. The urea melt enters the dome preferably with a temperature between 135 and 250° C. The interface between the reactor body and the dome can be designed such that it is partially or completely open e.g. the interface can be either covered by a bubble cap tray, a sieve tray or alike or it can be completely free of any cover. In any case, a continuous stream of urea melt from the dome into the first compartment and a continuous stream of offgases from the first compartment into the dome have to be guaranteed.

The dome comprises preferably a cylindrical top. The cross section of the dome has to be specified with respect to the gas velocity. The gas velocity in turn should be low enough to allow settling of the urea droplets and/or the melamine carryover from the offgas stream. In general, the dome can have a diameter between 1 m and 5 m, preferably between 1 m and 3 m, in particular preferably between 1 m and 2 m. The height of the dome can be between 1 and 10 m, preferably 3 and 8 m, in particular preferably between 4 and 6 m.

In one exemplary embodiment of the present invention at least one of the two compartments, preferably the compartment used for melamine synthesis, of the horizontal reactor body comprises at least one heating element. The heating element can be heated by molten salt, thermal oil or alike. Said compartment can also comprise an inlet, like an injector or a nozzle, for feeding additional compounds, in particular ammonia into the synthesis section.

The pressure in the synthesis area is between 5 and 20 MPa, preferably between 8 and 15 MPa in dependence of the reactor temperature. The temperature in the synthesis compartment or part of the reactor is—depending on the applied pressure—between 330 and 450° C., preferably between 330 and 400° C., in particular preferably between 330 and 380° C. In this respect it is important that the temperature at the prevailing pressure is high enough for keeping the melamine melt in the molten state in order to avoid blocking.

Between the melamine synthesis compartment of the reactor body and the dome, in particular the connecting area between both, bubble cap trays, sieve trays or similiar structures are preferably arranged for improving the separation effect of the offgases and preventing melamine melt entering the dome zone. Thus, only a reduced amount of melamine melt can reach the dome and solidification of melamine is avoided.

In another exemplary embodiment of the invention at least a second of the two compartments, preferably the compartment used as a stripper unit, comprises at least one inlet for gaseous ammonia and at least one outlet for melamine melt. In general, the ammonia gas should be fed with a pressure which is somewhat higher than the pressure in the stripper compartment. The flow rate of the ammonia gas should be high enough to minimize $CO^2$ solubility in the melamine melt. The temperature and pressure in the stripping compartment are basically the same as in the synthesis compartment.

The ammonia inlet comprises preferably multiple nozzles, which are arranged along the lower side of the body reactor in the lower part of the stripping compartment. The ammonia inlet may also be constructed in form of a distribution plate having openings or alike. Thus, an even distribution of ammonia gas over the whole stripping compartment is guaranteed. The nozzles or openings are dimensioned in such a manner that a fine distribution of the ammonia gas in the melamine melt is guaranteed. This in turn provides an intensive and homogenous mixing and therefore enables good and almost quantitative removal of offgases.

The at least two compartments of the reactor body are separated by the at least one baffle such that the synthesis compartment can comprise at least one half, preferably two thirds of the horizontal reactor and the stripping compartment can comprise up to one half, preferably one third of the volume of the reactor. However, it could also be conceivable that both compartments have almost the same volume. In general, the volume of the horizontal reactor and thus the volume of the two compartments have to be specified according to the residence time that is necessary to complete the reactions.

In another exemplary embodiment of the invention the height of the at least one baffle is at least one third, preferably between two thirds and three quarters of the height of the horizontal reactor.

The baffle is preferably designed as an overflow baffle. It is also conceivable that more than one baffle is placed in the reactor whereby the multiple baffles can be of different heights, respectively. The baffle is arranged is the reactor such that the synthesis compartment comprises about two thirds of the horizontal reactor and the stripping compartment about one third of the reactor volume.

The dimensions of the reactor depend on the overall plant capacity and on the operating pressure which should be between 5 and 20 MPa. The individual compartments have to be designed such that volumes, exchange surface, residence times of the fluid, the flow rates of the fluids, the maximum pressure drops for the reactor operation are easily adapted and guarantee the optimal performance of the reactor.

The process for obtaining melamine from urea at high pressure in a reactor according to the invention comprises the steps of feeding liquid urea into the at least one dome of the reactor, heating the liquid urea in the at least one first compartment of the reactor, separating the offgases from thus obtained melamine melt by releasing the offgases through the dome, transferring the melamine melt obtained in the at least one first compartment over the at least one baffle into the at least one second compartment of the reactor, feeding gaseous ammonia into the at least one second compartment of the reactor, and releasing the thus stripped melamine melt from the at least one second compartment. The melamine flow through the reactor is driven by the pressure difference between the reactor and the downstream equipment.

The dome operating as a scrubber compartment performs the following functions: the fed urea melt is pre-heated, and the offgases from the melamine synthesis are cooled and washed such that any melamine present in the offgases is removed. The urea melt enriched with melamine and a certain amount of the offgas is passed by gravity into the first compartment of the reactor where melamine synthesis occurs.

The urea melt enters the dome with a temperature between 135 and 160° C. The offgases ascending from the synthesis and the stripping compartment heat the urea melt to a temperature between the inlet temperature and the reaction temperature, for instance to a temperature between 200 and 250° C. At the same time the ascending offgases are cooled down and are discharged with a temperature above 200° C. The temperature difference of the gas and liquid is small due to the intensive contact of gas and liquid in the packing. A heat exchanger is used to adjust the gas and liquid temperature. The excess heat serves for steam generation in a heat exchanger. The cooled offgases are finally released on the top of the dome through an outlet, for instance a pressure control valve.

The urea melt descends through the dome into the first compartment of the reactor, where it is heated to a reaction temperature between 330 and 450° C., preferably between 330 and 400° C., in particular preferably between 330 and 380° C. The temperature depends on the applied pressure which is between 5 and 20 MPa, preferably between 8 and 15 MPa.

Urea is converted to melamine in this first compartment. The heat required is supplied by a heating bundle which is preferably operated with molten salt or thermal oil.

The offgas generated in the course of the reaction ascend through the reaction mixture into the dome whereby causing high turbulence of the melamine melt and thus at least a partial circulation of the melamine melt. In addition, the temperature gradient between the heating bundle and the melamine melt contribute to the natural recirculation of the reaction melt in the synthesis compartment.

The offgases, in particular $NH_3$ and $CO_2$ formed during the melamine reaction, are separated in a continuous manner from the reaction melt. As described above, the offgases ascend into the dome, are cooled there and released through at least one outlet, for instance a pressure control valve. A continuous offgas-stream into the dome is guaranteed due to the upward flow of the offgases, whilst the liquid urea melt flows downwards.

Following the urea conversion to melamine the melamine melt flows over the at least one baffle into the second compartment e.g. stripping compartment of the reactor. This second compartment which serves as a stripping compartment may fulfil at least two functions. The gaseous products, in particular $NH_3$ and $CO_2$, are removed from the melamine melt and the melamine melt is allowed to reside (Aging). During this Aging-phase melamine resides in the second compartment of the reactor in the presence of an excess of ammonia to allow partial conversion of deammonisation products into melamine.

In order to do so gaseous ammonia is fed into the second compartment. The ammonia is fed through a suitable inlet, in particular through a distributor, injector or nozzle. Before entering the second compartment of the reactor through the inlet the gaseous ammonia is preheated to a temperature above 330° C. The limiting factor for temperature of ammonia gas is the risk of solidification of the melamine melt, e.g. the ammonia temperature must be high enough so that the melamine does not solidify and does not block the nozzles.

The stripped melamine melt may finally leave the reactor through at least one suitable outlet, in particular a pressure control valve, for further work up.

The present invention is further explained in more detail based on the following examples in conjunction with the Figures.

DETAILED DESCRIPTION OF THE INVENTION

Figure 1:
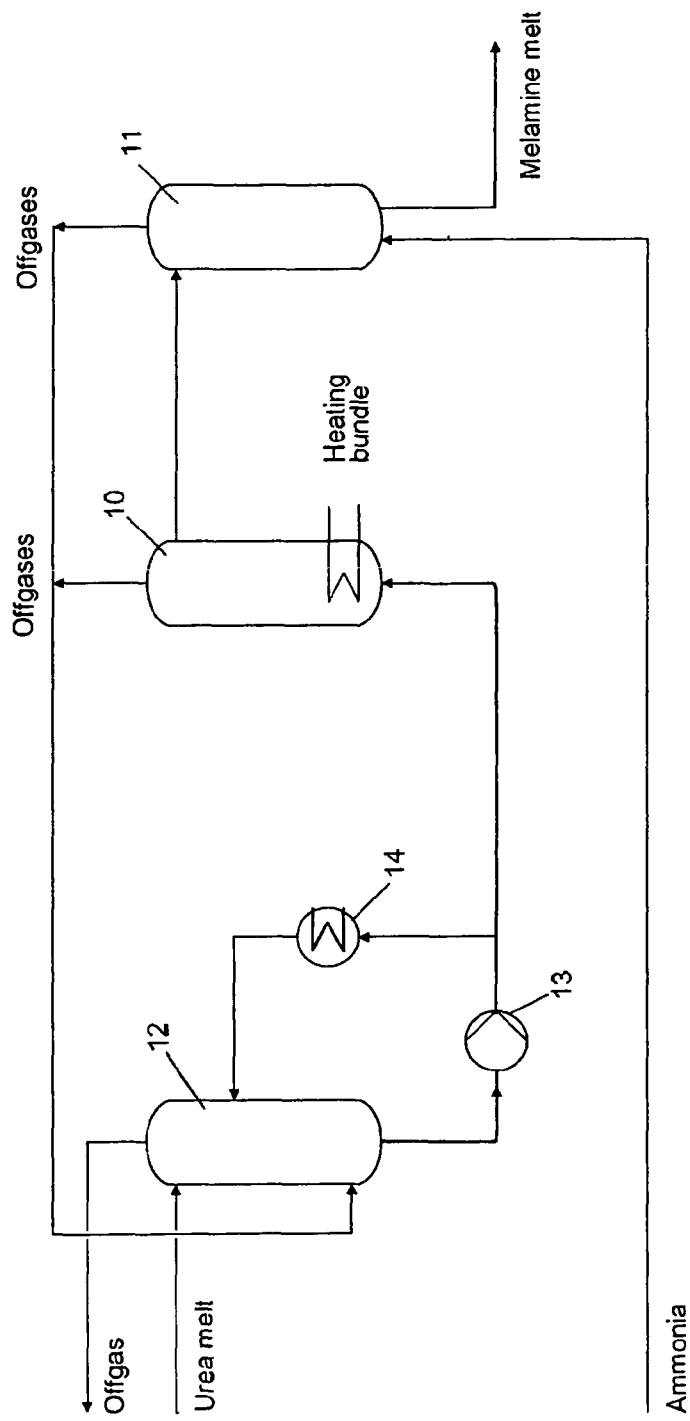
FIG. 1 a scheme of a conventional high-pressure melamine synthesis reactor according to prior art, and FIG. 2 a schematic view of a high-pressure melamine synthesis reactor according to an embodiment of the invention.

FIG. 1 shows a scheme of a conventional high-pressure part of a melamine synthesis plant. The high-pressure part consists basically of a synthesis reactor 10 as a first reactor, a stripping reactor 11 as a second reactor and a scrubber 12.

The conversion of urea to melamine is carried out in the synthesis reactor 10 which is equipped with heating bundles. The obtained raw melamine melt is then transferred to the second reactor or stripping reactor 11 in which the residual gases are removed from the melamine melt by introducing gaseous ammonia in counter current, and where the melamine melt is allowed to reside for a certain time (Aging). The offgases are removed from the stripper 11 and sent to the scrubber 12 where the offgases are cooled and the urea melt is preheated. The urea melt comprises fresh urea or circulating urea which is kept in circulation by a circulation pump 13. The excess heat in the scrubber is removed by an external heat exchanger 14.

Figure 2:
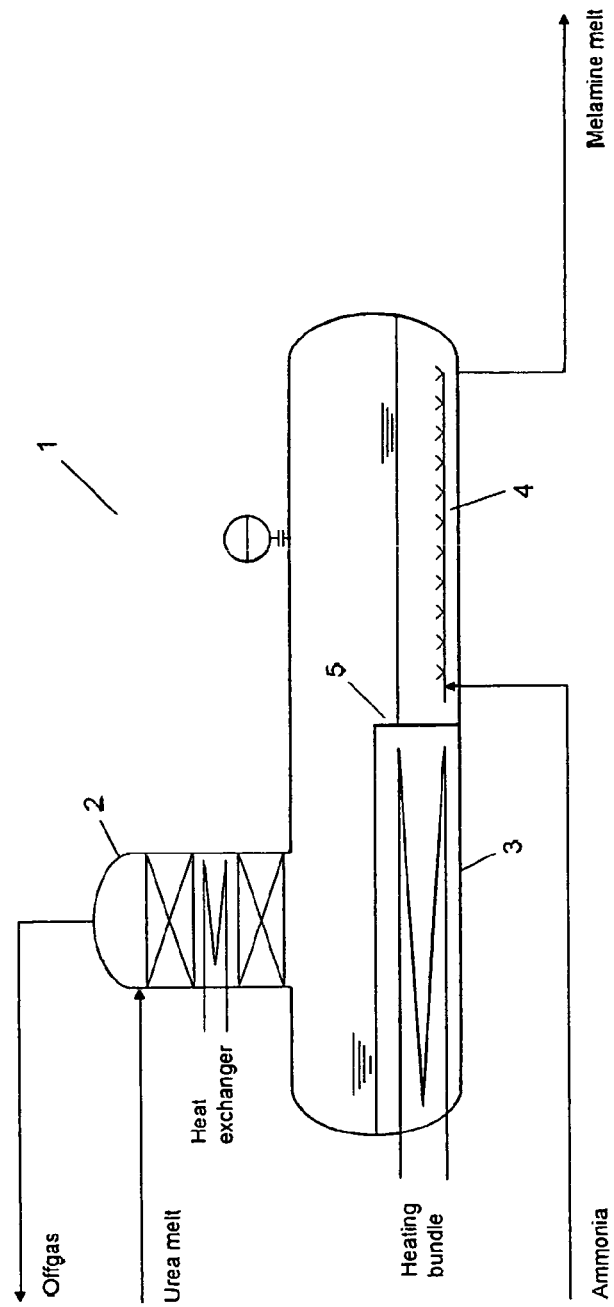

FIG. 2 shows a high-pressure reactor 1 according to the invention. The reactor 1 comprises essentially a dome 2, a melamine synthesis compartment 3 and a stripping compartment 4, the two compartments separated by an overflow baffle 5.

Example

A horizontal reactor that produces 50,000 tons per year of melamine has the following approximate dimensions. The reactor has a diameter of 2 m and a length of 10 m. The dome has a diameter of 1.80 m and a height of 5 m. The baffle has a height of 1.50 m and separates the reactor at 7.50 m so that the volume of the synthesis compartment comprises of three quarters of the total reactor volume.

Urea enters the dome of the reactor at 150° C. and is preheated by the offgas, and melamine impurities in the offgas are washed out. The excess heat is removed by a heat exchanger that generates steam. The purified offgas is discharged from the reactor with a temperature of approx. 200° C.

The temperature in the reactor is 370° C. and the pressure is 10 MPa. In the synthesis compartment, urea reacts to a melamine melt. The heat of reaction is supplied by a heating bundle that operates with molten salt. Offgas is generated at the heating bundle and enhances turbulence and heat transfer of the heating bundle to the melamine melt. The offgas ascends to the surface of the melamine melt and is liberated there.

When the synthesis compartment is full with molten melamine, it flows over the baffle to the stripping compartment. Ammonia at 400° C. and 10.5 MPa is fed to the stripping compartment and strips dissolved $CO_2$ from the melamine melt. The level in the stripping compartment is controlled by a valve at the outlet of the reactor that adjusts the flow of the melamine melt. Thus, residence time in the stripping compartment and the degree of aging can be controlled within the limits that are set by the reactor geometry.

The thus obtained melamine has a purity of at least 99.8%.

The invention claimed is:

1. A high-pressure melamine reactor comprising:
at least one horizontal reactor body having a bottom and a top side with at least one dome integrally formed on the top side of the reactor body, wherein
the at least one horizontal reactor body comprises at least two compartments separated by at least one baffle,
the at least one dome is solely located above at least one of the compartments serving as a melamine synthesis unit,
the at least one compartment serving as a melamine synthesis unit comprises at least one heating element, and
the at least one dome comprises at least one inlet for urea melt, at least one outlet for offgas and at least one heat exchanger.

2. The reactor according to claim 1, wherein the at least one dome serves as a scrubber unit.

3. The reactor according to claim 1, wherein a second of the compartments serves as a stripping unit.

4. The reactor according claim 1, wherein the dimensions of the dome correspond to the dimensions of the compartment serving as the melamine synthesis unit such that the dome covers fully or at least partially said compartment.

5. The reactor according to claim 1, wherein the dome has a diameter between 1 m and 5 m, or between 1 m and 3 m, or between 1 m and 2 m.

6. The reactor according to claim 1, wherein the at least one dome has a height between 1 and 10 m, or between 3 and 8 m, or between 4 and 6 m.

7. The reactor according to claim 1, wherein a second of the least two compartments serves as stripping unit and comprises at least one inlet for gaseous ammonia and at least one outlet for melamine melt.

8. The reactor according to claim 1, wherein the at least one compartment serving as melamine synthesis unit comprises at least one half of the volume of the horizontal reactor and a second compartment serving as stripping unit comprises up to one half of the volume of the horizontal reactor.

9. The reactor according to claim 1, wherein the height of the at least one baffle is at least one third of the reactor body height.

10. A process for obtaining melamine from urea at high pressure in a reactor according to claim 1 comprising the steps of:
feeding liquid urea into the at least one dome of the reactor,
heating the liquid urea in the at least one compartment of the reactor,
separating the offgases from thus obtained melamine melt by releasing the offgases through the at least one dome
transferring the melamine melt obtained in the at least one compartment over the at least one baffle into at least one second compartment of the reactor;
feeding gaseous ammonia into the at least one second compartment of the reactor, and
releasing the thus stripped melamine melt from the at least one second compartment.

11. The process according to claim 10, wherein a temperature in the reactor is between 330 and 450° C. and a pressure is between 5 and 20 MPa.

12. The process according to claim 10, wherein a temperature of the gaseous ammonia feed into the second compartment of the reactor is above 330° C.

* * * * *